(12) United States Patent
Vahala et al.

(10) Patent No.: US 10,974,070 B2
(45) Date of Patent: Apr. 13, 2021

(54) MEDICAL PRODUCT CONFIGURED TO BE USED FOR IMAGE BASED RADIOTHERAPY PLANNING

(71) Applicant: KONINKLIJKE PHILIPS N.V., Eindhoven (NL)

(72) Inventors: Erkki Tapani Vahala, Hyvinkaa (FI); Kumar Raja Gattamaneni, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 111 days.

(21) Appl. No.: 16/323,816

(22) PCT Filed: Aug. 11, 2017

(86) PCT No.: PCT/EP2017/070515
§ 371 (c)(1),
(2) Date: Feb. 7, 2019

(87) PCT Pub. No.: WO2018/029368
PCT Pub. Date: Feb. 15, 2018

(65) Prior Publication Data
US 2019/0209862 A1 Jul. 11, 2019

(30) Foreign Application Priority Data

Aug. 11, 2016 (IN) .............................. 201641027404
Sep. 29, 2016 (EP) ..................................... 16191485

(51) Int. Cl.
*A61N 5/10* (2006.01)
*G16H 30/20* (2018.01)
(Continued)

(52) U.S. Cl.
CPC ............ *A61N 5/1039* (2013.01); *A61B 5/055* (2013.01); *A61B 6/032* (2013.01); *A61B 6/037* (2013.01);
(Continued)

(58) Field of Classification Search
CPC ....... A61N 5/103; A61N 5/1039; A61B 6/032
(Continued)

(56) References Cited

U.S. PATENT DOCUMENTS

2004/0165696 A1 8/2004 Lee
2007/0078306 A1 4/2007 Allison et al.
(Continued)

FOREIGN PATENT DOCUMENTS

| WO | WO-2007014092 A2 * | 2/2007 | ............. A61N 5/103 |
|----|---------------------|--------|-------------------------|
| WO | WO-2012035463 A1 * | 3/2012 | ................ G06T 7/12 |
| WO | WO-2012045163 A1 * | 4/2012 | ............. A61N 5/103 |

OTHER PUBLICATIONS

Rajasekar et al "A Grapical User Interface for Automatic Image Registration Software Designed for Radiotherapy Treatment Planning" Medical Dosimetry, Elsevier US, vol. 29, No. 4, Jan. 1, 2004 p. 239-246.

*Primary Examiner* — John P Lacyk
(74) *Attorney, Agent, or Firm* — Sherry Austin

(57) ABSTRACT

It is an object of the invention to improve the radiotherapy workflow. This object is achieved by a medical product configured to be used for image based radiotherapy planning. The medical product is configured to be connected to: —a medical imaging system configured for acquiring medical images of a patient; —a contour module configured for segmenting one or more contours based on one or more of the medical images and; —a treatment planning system configured for calculating a radiotherapy plan based on the one or more contours. The medical product comprises a user
(Continued)

interface configured to receive user input on a treatment target in the patient and to receive user input on a treatment technique. The medical product is configured to execute a data object readable to the medical imaging system, the contour module and the treatment planning system on the basis of the user input and wherein the data object comprises computer readable instructions for these systems and modules and wherein the systems and modules are configured to contribute to the creation of the radiotherapy plan based on the user input.

18 Claims, 4 Drawing Sheets

(51) Int. Cl.
*A61B 5/055* (2006.01)
*A61B 6/03* (2006.01)

(52) U.S. Cl.
CPC ............. *A61N 5/103* (2013.01); G16H 30/20 (2018.01); *A61N 2005/1074* (2013.01)

(58) Field of Classification Search
USPC ........................................................ 600/1–8
See application file for complete search history.

(56) References Cited

U.S. PATENT DOCUMENTS

| | | |
|---|---|---|
| 2007/0189591 A1 | 8/2007 | Lu et al. |
| 2010/0104068 A1 | 4/2010 | Kilby et al. |
| 2012/0203053 A1 | 8/2012 | Kilby et al. |
| 2013/0272593 A1 | 10/2013 | Lee et al. |
| 2013/0289332 A1 | 10/2013 | Purdie et al. |
| 2013/0301893 A1 | 11/2013 | Netsch et al. |
| 2018/0318604 A1* | 11/2018 | Schadewaldt ........ A61N 5/1039 |

* cited by examiner

MEDICAL PRODUCT CONFIGURED TO BE USED FOR IMAGE BASED RADIOTHERAPY PLANNING

CROSS REFERENCE TO RELATED APPLICATIONS

This application is a U.S. national phase application of International Application No. PCT/EP2017/070515, filed on Aug. 11, 2017, which claims the benefit of IN Application Serial No. 201641027404 filed on Aug. 11, 2016 and EP Application Serial No. 16191485.8 filed Sep. 29, 2016, both of which are incorporated herein by reference.

FIELD OF THE INVENTION

The invention relates to the field of medical systems and products and more specifically the invention relates to the field of radiotherapy.

BACKGROUND OF THE INVENTION

The current radiotherapy workflow is a time intensive workflow. After a patient has been diagnosed with cancer and it has been decided that radiotherapy is the treatment of choice, one or more medical images will be acquired from the patient. These medical images will be used to determine a location of a treatment target (tumour) and organs at risk within the patient. Once all medical images have been acquired, the treatment target and organs at risk will be delineated within the medical images. The most widely used medical images for this purpose are computed tomography (CT) images. However, magnetic resonance images (MRI) or positron emission tomography (PET) images could be of added value, especially for delineating the treatment target. It may be favourable in some situations to replace the CT images entirely by MRI images.

Also, one or more of these medical images will be used in order to determine how radiation will be attenuated within the patient. Radiation attenuation can be directly determined from CT images. However, when using MRI images for this, more elaborate images processing will be needed.

After the treatment target(s) (e.g. prostate and seminal vesicles) and organs at risk have been delineated and the information about radiation attenuation has been obtained, a treatment technique will be selected. This treatment technique comprises for example information about what treatment device is being used, dose prescriptions for the treatment target(s) and dose constraints for organs at risk, clinical goals for the treatment target and/or organs at risk, a method that will be used for the treatment, e.g. intensity modulated radiotherapy (IMRT) or volumetric modulated arc therapy (VMAT) and a number of treatment fractions.

After the treatment technique has been selected, treatment planning can be started. Based on the resulting treatment plan the patient will be treated. This total workflow easily takes 4-8 hours, or even more, depending on the complexity of the case.

SUMMARY OF THE INVENTION

It is an object of the invention to improve the radiotherapy workflow. This object is achieved by a product according to A medical product configured to be used for image based radiotherapy planning further configured to be connected to:
 a medical imaging system configured for acquiring medical images of a patient;
 a contour module configured for segmenting one or more contours based on one or more of the medical images;
 a treatment planning system configured for calculating a radiotherapy plan based on the one or more contours and;
 the medical product comprising a user interface configured to receive user input on a treatment target in the patient and to receive user input on a treatment technique, wherein the medical product is configured to execute a data object readable to the medical imaging system, the contour module and the treatment planning system on the basis of the user input and wherein the data object comprises computer readable instructions for these systems and modules and wherein the systems and modules are configured to contribute to the creation of the radiotherapy plan based on the user input.

It is an insight of the inventors that the radiotherapy workflow can be largely simplified if the treatment technique is already selected prior to the acquisition of the medical images. This selection of the treatment technique will then affect all following steps from image acquisition parameters, to (auto)contour parameters and treatment planning parameters. Also it may affect review options. These review options for example determine how images or results can be viewed by a user. This in turn may depend on the contour module, viewing station or planning system used by the user. It is a further insight of the inventors that when in addition to parsing only data from one system to the other also logic will be parsed. This may pave the road for simplifying workflow. At present this logic is hard coded in the different systems and modules. Parsing logic to the systems can be done by means of so-called "Therapy cards". Also carrying the composite data can be done by means of a Therapy-card. A therapy card can be implemented in many ways e.g. it can be a blob of byte data transferred from one network node to another and manifests as a file on each or some of the nodes—it can also be a reference to an object that resides on a central server and each node manipulates the object remotely (e.g., using a RESTful application programming interface or DICOM Q/R, Store, and/or Worklist services). By means of the invention, the long existing and time consuming workflow can be easily automated and simplified.

According to further embodiments of the invention, no user interaction will be needed or allowed between the start of image acquisition and the finishing of the radiotherapy plan. In this way the amount of man hours spend on the workflow can be greatly reduced. According to further embodiments of the invention, the radiation oncologist can receive an alert, e.g. by means of email, instant message application, or a tablet/desktop application linked to DICOM worklist service class provider, that the treatment plan is ready and needs to be checked.

According to further embodiments, a user, e.g. the radiation oncologist, receives an alert when certain information is missing, as this lack of information may cause increased waiting times for the patient. For example the user may be alerted when a certain image has not been acquired, whereas the patient is scheduled for treatment in the near future.

According to another embodiment of the invention, the medical product can be configured to allow user adaptation and/or review of the automatically generated registrations, delineations or contours, for example either as a static configuration option or a dynamic, cases-by-case user-selectable or automatically set option, for example, at the time of initial prescription, or at the scanner. This embodiment is advantageous, because in this way the user can alternate between different workflows depending on the difficulty of the treatment and the level of automation available to assist in treatment plan generation.

According to embodiments of the invention, the (auto) contour parameters could be parameters that steer auto contouring. In addition or alternatively these parameters could describe the names of the structures to be delineated and/or the colours to be used for this delineation. This will lead to improved standardization and thereby may reduce the chance that errors will be made.

According to further embodiment of the invention, the therapy card can carry screen layout, or editing tool settings to automate steps at the review and user adaptation stages. Also, the user interface can be configured to receive user input about patient positioning, user interface tooling and/or view layout selections or templates thereof, In this way, the medical product can be customized to work with different viewing stations or planning software. The medical product (therapy card) can also enable storing of registration instructions to pull in and display data from multiple sources, e.g., PET, MRI, and CT, to represent data in a manner that is beneficial for use adaptation/or review.

According to further embodiments of the invention, the medical imaging product comprises a magnetic resonance system configured for acquiring one or more magnetic resonance images and the medical product is further configured to be connected to an attenuation map generation module configured to calculate an attenuation map based on one or more of the magnetic resonance images and the treatment planning system is configured for calculating a radiotherapy plan based on the attenuation map provided by the attenuation map generation module. Another option for the attenuation map module is to (deformably) register CT and MRI images in the case this is used in a workflow where MRI is used to augment CT-based treatment with better soft-tissue contrast contours. CT+PET(+MRI) would also need the module for registration. This embodiment is advantageous, because it supports a fully MRI based workflow. This is advantageous, because this can result in a better delineation of the treatment target, while avoiding image registration errors occurring from the registration of CT and MRI images. Also, radiation to the patient can be reduced with eliminating CT from the planning process.

According to further embodiments of the invention, the data-object, e.g., a file, volatile memory object, or (possible remotely accessible) database entity comprises instructions for the MRI system to acquire Dixon images and T2w images and data-object further comprises instructions for the contour module to segment the one or more contours based on an in-phase Dixon and a T2w image and the data object further comprises instructions for the attenuation map generation module to create an attenuation map based on the Dixon images. This embodiment is advantageous, because by using some of the medical images for both contouring or delineating and creating an attenuation map less time can be spend on image acquisition, which in turn may result in less motion induced errors.

According to further embodiments of the invention, the data-object, e.g., a file, volatile memory object, or (possible remotely accessible) database entity comprises instructions for the MRI system to instruct the MRI technician to position the patient in treatment position, instructions for the medical imaging system to acquire medical images and instructions for the contour module to segment the one or more contours and optionally instructions for the attenuation map generation module to create an attenuation map based on the one or more medical images. The data object further comprises instructions for the treatment planning system to create a treatment plan with given or referenced optimization goals. This embodiment is advantageous, because by showing positioning instructions and using some of the medical images for both contouring or delineating and creating an attenuation map less time can be spend on patient handling and image acquisition, which in turn may result in less motion induced errors. Combining the treatment plan setup and generation instructions to the data is advantageous, because it allows optimization of the imaging for the subsequent treatment plan generation, e.g., by limiting the field of view in images and contouring to those organs at risk that are pertinent for the treatment, which in turn reduce the image acquisition times. According to further embodiments of the invention the medical product is configured to adapt the instructions based on an output of one of the systems or modules. This is advantageous as it may result in an improved treatment plan or more efficient workflow. Examples of this could be 1. if image quality is not sufficient diverge to manual contouring 2. if a certainty achieved by the (auto)contouring module is sufficient a treatment plan for hypofractionation could be created, whereas a more standard treatment plan will be created if (auto)contouring appears to be more challenging. 3. based on functional image, like e.g. diffusion weighted or PET images it could be decided to include a boost volume in the treatment plan. According to further embodiments of the invention, the treatment planning system is instructed to calculate multiple plans, e.g. a reference plan according to instructions of the user and an adapted plan, e.g. according to embodiments described above. Another option could be that multiple variants of a plan are calculated from which the user can choose. This embodiment is advantageous, because the user is given the opportunity to review multiple plans and decide for the best option. This is also an enhancement of the workflow which enables reliable plan generation.

According to further embodiments of the invention, the medical product is configured to provide for instructions to reacquire one or more of the medical images based on segmentation results provided by the contour module and/or based on a quality of the attenuation map generated by the attenuation map generation module. For example, the medical product can be configured to parse the therapy card logic at the imaging modality during the start of a lengthy algorithm (e.g., auto-contouring algorithm or pseudo-CT generation from MRI data). The logic can provide an early warning signal to the technician if the initial checks or preprocessing algorithms detect invalid patient position, patient movement, or other artifacts that are recoverable but likely to cause algorithm failures. This allows the technician to re-scan the patient within the imaging session. This embodiment is advantageous, because by immediately starting the contour module and checking whether contouring with sufficient quality is possible, it can be circumvented that a patient will need to be rescanned or will receive a suboptimal treatment.

These and other aspects of the invention will be apparent from and elucidated with reference to the embodiments described hereinafter.

DETAILED DESCRIPTION OF THE EMBODIMENTS

Figure 1:
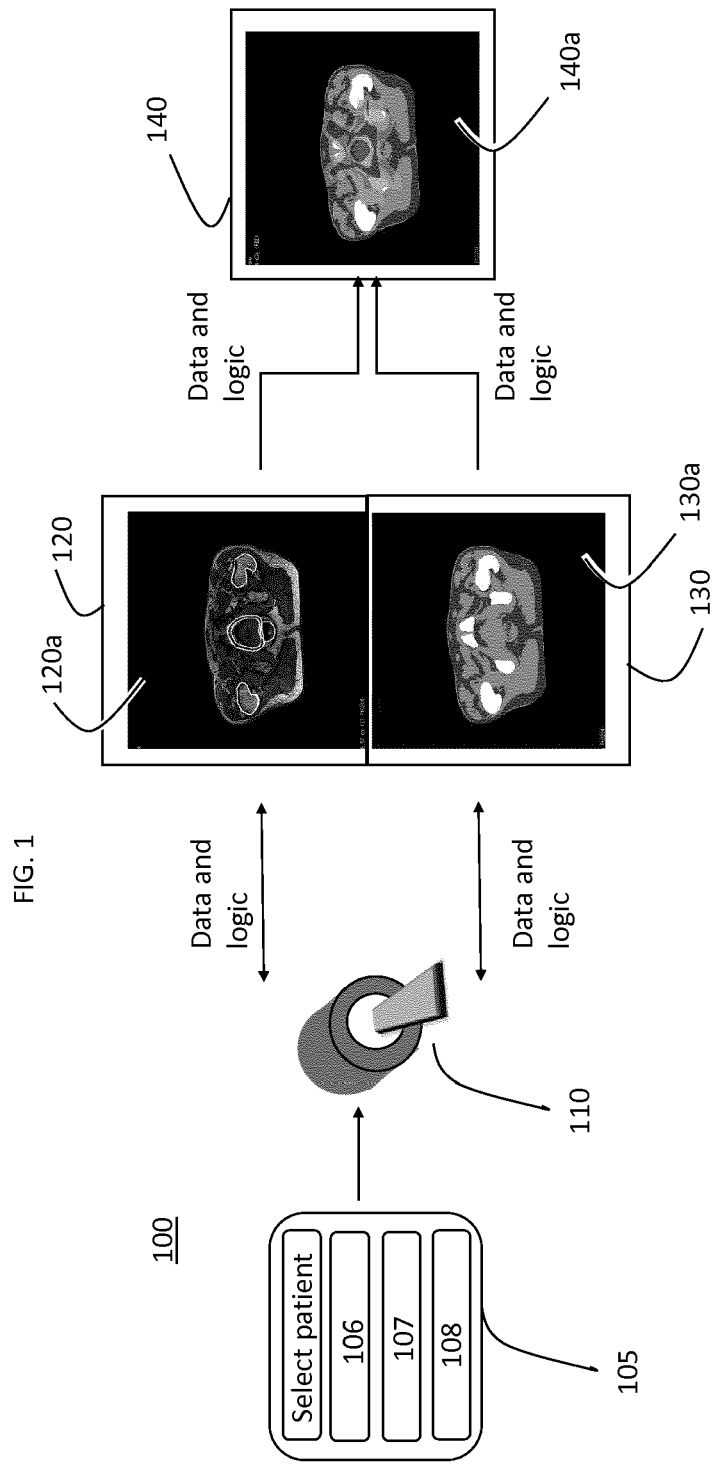
FIG. 1 diagrammatically shows a medical product according to embodiments of the invention and FIG. 2 diagrammatically shows a user interface that can be used in embodiments of the invention and FIG. 3 diagrammatically shows a medical product according to embodiments of the invention and FIG. 4 diagrammatically shows a user interface that can be used in embodiments of the invention.

FIG. 1 diagrammatically shows a medical product according to embodiments of the invention. The medical product comprises a user interface 105. In the user interface a patient can be selected. In addition, the user interface is configured to receive user input on a treatment target 106 in the patient and to receive user input on a treatment technique 107. This selection may automatically determine one or more parameters for the following workflow. These parameters could be for example what structures to delineate, e.g. for treatment and/or organs at risk, what margins to use and/or what dose constraints should be used. Alternatively, these one or more of these parameters could be specified by the user in the user interface 108. Also, the medical product could deduce some of these parameters automatically based on patient information, like e.g. tumor stage, number and/or location of positive biopsy cores, tumor specific markers, patient age. The treatment technique could comprise for example information about the treatment device used (e.g. linac, proton therapy etc.) as well as which of the specific treatment devices in the hospital will be used (e.g. linac number 3), whether e.g. conformal, IMRT or VMAT treatment will be used. The medical product could be further configured to receive user input about patient positioning, user interface tooling and/or view layout selections or templates thereof 108. User interface tooling and/or view layout selections determine the lay-out of viewing settings on a viewing station and/or the treatment planning system.

The product is configured to be connected to one or more medical imaging systems 110. Examples of such medical imaging systems could be CT, MRI, ultrasound, PET, SPECT. A combination of medical imaging systems could be also advantageous, as some medical imaging systems could be used for acquiring images suitable to be used for delineation of a body contour or organs at risk (e.g. CT and MRI), whereas other medical imaging systems could be used to delineate or characterize a tumor inside a patient (e.g. MRI or PET). This in turn may affect boost volume and/or dose applied to the tumour. The medical product is configured to translate the user input to relevant instructions for the medical imaging system. The user may have specified what images need to be acquired. However, more preferably the medical product automatically derives this based on the selected treatment target and maybe also the treatment technique. For example when the prostate is selected as a treatment target, the file executed by the medical product may comprise instructions for a magnetic resonance imaging system to acquire Dixon images and T2w images for contouring and generating an attenuation map. The data object may further comprise instructions to acquire a diffusion weighted image, which could later be used to define a boost volume within the prostate. The user may have also specified patient positioning instructions for the treatment, which can be incorporated into the file to be shown to the user at the correct time in the scanning workflow.

The medical product is configured to parse relevant medical images from the medical imaging system to the contour module 120. The contour module is configured for segmenting one or more contours based on one or more of the medical images. Image 120a shows an example of an output of the contour module 120. In image 120a for example the prostate and the rectum are segmented. In addition to the medical images, the relevant user input is provided to the contour module. For example if the prostate is selected as a treatment target, the medical product may automatically deduce from that that the prostate and e.g. the rectum and bladder need to be delineated. Depending on the selected treatment technique the seminal vesicles and/or lymph nodes may or may not be included in the target volume. Also depending on the selected treatment technique some additional medical images may be provided to the contour module in order to be able to define a boost volume (e.g. a DWI or PET image may be provided). Further more specifically, the file provided by the medical product to the contour module may comprise instructions for the contour module that determine what contours should be segmented on what image, e.g. segment one or more contours based on an in-phase Dixon and a T2w image. The medical product could provide instructions that allow (potentially based on detected quality of the medical images) a user to manually create or adapt contours. However, preferably the contouring is performed automatically.

The contour module 120 could be run while the patient still is in the medical imaging system. In that case, the medical product could be configured to provide feedback from the contour module to the medical imaging system. This feedback could be used to instruct the medical imaging system to reacquire certain medical images. For example, the medical product can be configured to parse the therapy card logic at the imaging modality during the start of a lengthy algorithm (e.g., auto-contouring algorithm or pseudo-CT generation from MRI data). The logic can provide an early warning signal to the technician if the initial checks or preprocessing algorithms detect invalid patient position, patient movement, or other artifacts that are recoverable but likely to cause algorithm failures. This allows the technician to re-scan the patient within the imaging session.

If the medical product is used in an MRI based workflow, the medical product could be configured to provide instructions to an attenuation map generating module 130. The attenuation map generating module is configured to calculate an attenuation map based on one or more of the magnetic resonance images. Image 130a shows an example of an attenuation map generated by the attenuation map generating module 130. The method for generating the attenuation map may be made dependent of the treatment target selected by the user.

The medical product is further configured to provide the medical images, the segmented contours and the attenuation map to the treatment planning system 140 The treatment planning system is configured for calculating a radiotherapy plan based on the one or more contours. Image 140a shows an example of a planned dose distribution as planned by the treatment planning system. Further the medical system is configured to translate the user input into instructions for the treatment planning system. Optionally, these instructions could in addition depend on one or more of the outputs of the medical imaging system or other modules. For example image quality, uncertainty in the segmentations and/or in the attenuation map could be used as an input for the treatment planning system. These uncertainties could be used by the treatment planning system when creating the treatment plan. For example, this could be used by including extra margins. Also the medical product could be configured to deviate from the selected treatment technique, e.g. if a image quality of a certain medical image based on which a boost volume is to be defined is not sufficient, the medical product could be configured to override the instructions and change the treatment technique to a treatment without the inclusion of a boost volume. Also if based on certain images it appears that the tumor is more advanced than expected, the treatment technique may be changed, for example the dose constraints may be changed or the target volume could be changed, e.g. the seminal vesicles could be included into the target volume. Optionally, in this case the treatment planning system may be instructed multiple plans, one treatment plan based on the user input and one adapted plan. Optionally, if the treatment plan is finished, the user, e.g. a physician will be alerted such that he can check the treatment plan and the contours. Also, optionally the system could provide the user with information where it has deviated from the user input or from a preferred scenario of the user. The medical product could be configured such that user interaction is allowed, e.g. for contouring. However, preferably the medical product is configured such that user interaction is no longer allowed after the start of acquisition of the medical images.

Figure 2:
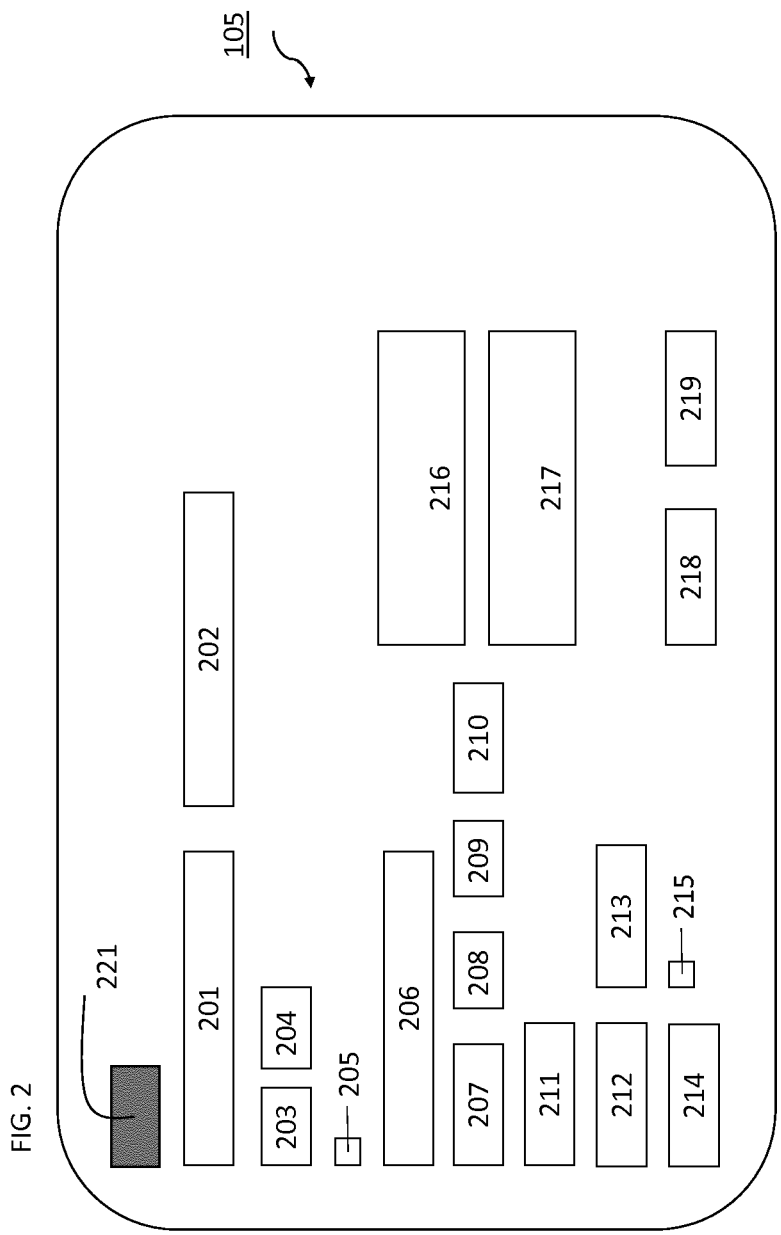

FIG. 2 diagrammatically shows a user interface that can be used in embodiments of the invention. In the user interface 105, the patient demographics can be entered or can be taken from the oncology information or PACS system. For example a patient name 201, patient ID 202, a patient's weight 203 and/or a patient's sex 204 can be entered. Also, the user interface may allow input on whether a patient has implants. Presence of implants may affect the imaging technique or sequence. For example, an imaging technique or sequence may be used that is less sensitive to metal artifacts. In addition or alternatively, the presence of implants may affect the treatment planning algorithm, as radiation beams should preferably not be directed towards the implants.

In the user interface, the user may select a treatment technique 206. Alternatively, the treatment technique may be derived from the patient demographics. The treatment technique could for example be "VMAT Prostate". In more detail, a treatment technique may comprise a radiotherapy technique 207 (e.g. "VMAT"), a total dose 208 (e.g. 72 Gy), number of fractions 209 (e.g. 28) and the treatment machine 210. The treatment technique may be further described in an additional text box 216. The user may specify to who the reviewing of the treatment plan will be assigned to 211. The reviewer may also be automatically selected, e.g. based on a workload of different radiation oncologists. The date of the scan may be given 212 and also the imaging modality 213 (e.g. MRI). Also, an exam card may be selected 214. Alternatively, the medical product may select the exam card automatically based on the patient demographics and/or the treatment technique. The user interface may further comprise an option to select if autocontours should be generated. Alternatively, only the contour naming and colours could be provided. Patient positioning instructions could also be provided 217. Further, the user may provide input about which contour module is to be used and which person the contouring will be assigned to. Alternatively, the medical product may automatically select either one or both. When all necessary information has been provided the patient may be added to the queue 221.

Figure 3:
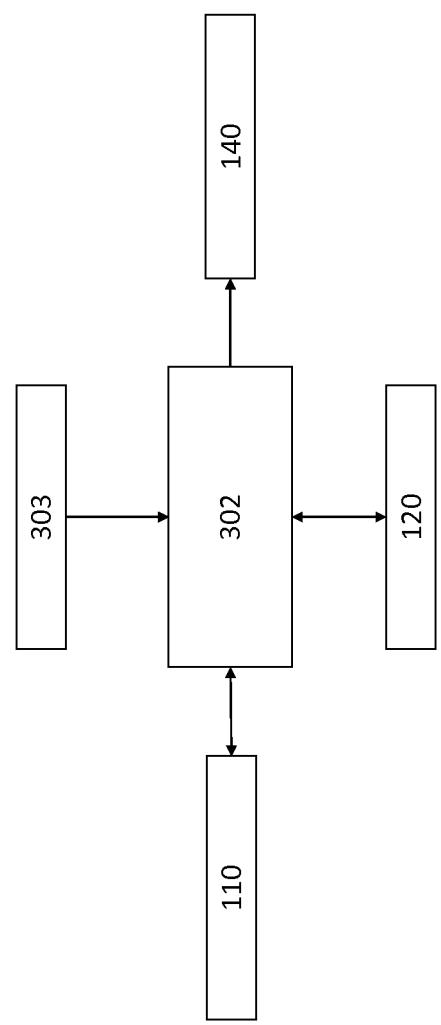

FIG. 3 diagrammatically shows a medical product according to embodiments of the invention. The oncology information system 303 may provide information (e.g. patient demographics, tumor stage etc) to the medical product 302. Based on the user input and/or the information from the oncology information system, the medical product may send imaging instructions to the medical imaging system 110. Based on the medical images acquired by the medical imaging system based on the instructions from the medical product and the user input, the medical product sends contouring instructions to the contour module 120. After contouring, the contour module will send the contours to the medical product, which will send these and the medical images to the treatment planning system 140 together with treatment planning instructions. Based on these inputs, the treatment planning system will create a treatment plan.

Figure 4:
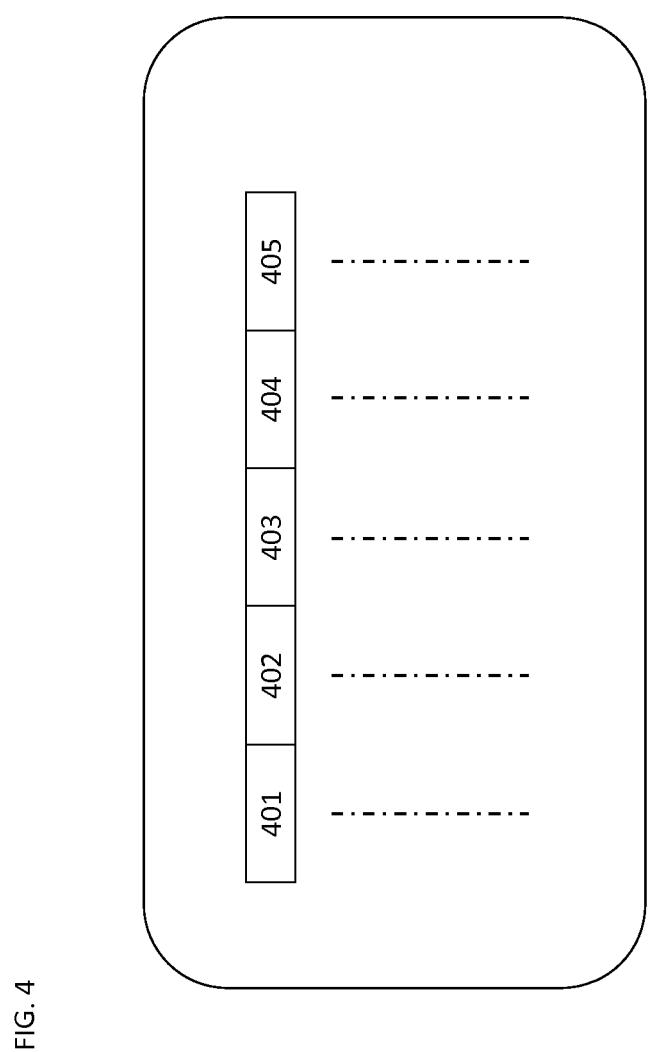

FIG. 4 diagrammatically shows a user interface that can be used in embodiments of the invention. This user interface can be used to monitor the process. It may show a patient ID 401, a patient name 402, a person responsible for the entire process or a specific task 403, the treatment technique used 404 and the status (e.g. "ready for review", "pending contouring", "pending imaging"). When the status is ready for review, the radiation oncologist may open the patient file and review the treatment plan.

Whilst the invention has been illustrated and described in detail in the drawings and foregoing description, such illustrations and description are to be considered illustrative or exemplary and not restrictive; the invention is not limited to the disclosed embodiments.

The invention claimed is:

1. A medical product for image-based radiotherapy planning by interfacing with a medical imaging system, a contour module, and a treatment planning system, the medical product comprising, a user interface configured to receive user input identifying a treatment target in a patient and a treatment technique for performing radiotherapy to treat the treatment target, and to provide a data object executable by the medical imaging system, the contour module and the treatment planning system, wherein the data object comprises computer readable instructions based on the treatment target and/or the treatment technique, the instructions comprising image acquisition parameters, contour parameters and treatment planning parameters, wherein the instructions are for the medical imaging system to acquire medical images of the patient according to the image acquisition parameters after the identifying of the treatment technique, for the contour module to segment one or more contours based on one or more of the medical images according to the contour parameters, and for the treatment planning system to calculate a radiotherapy plan based on the one or more contours according to the treatment planning parameters.

2. The medical product according to claim 1, wherein the user interface is further configured to allow user to review and/or adapt the one or more contours generated by the contour module.

3. The medical product according to claim 1, the radiotherapy plan is calculated based on the user input without a need for further user interaction.

4. The medical product according to claim 1, wherein the medical imaging system is a magnetic resonance system configured for acquiring magnetic resonance images as the medical images of the patient, wherein the medical product further interfaces with an attenuation map generation module configured to calculate an attenuation map based on one or more of the magnetic resonance images, and wherein the data object further comprises instructions for the treatment planning system to calculate the radiotherapy plan further based on the attenuation map provided by the attenuation map generation module.

5. The medical product as claimed in claim 4, wherein the data object further comprises instructions for the magnetic resonance imaging system to acquire Dixon images and T2w images, for the contour module to segment the one or more contours based on an in-phase Dixon and a T2w image, and for the attenuation map generation module to create the attenuation map based on the Dixon images.

6. The medical product as claimed in claim 1, wherein the instructions are adapted based on an output of at least one of the medical imaging system, the contour module, or the treatment planning system.

7. The medical product as claimed in claim 5, wherein the data object further comprises instructions for the medical imaging system to reacquire one or more of the medical images based on segmentation results provided by the contour module.

8. The medical product as claimed in claim 1, the treatment technique identified via the user interface is overruled based on one or more of the medical images of the patient.

9. The medical product as claimed in claim 1, wherein the data object further comprises instructions for registering the medical images in a rigid or non-rigid way prior to segmentation of the one of more contours.

10. The medical product as claimed in claim 1, wherein the medical imaging system is at least one of a group consisting of a computed tomography (CT) and a position emission tomography (PET) system.

11. The medical product according to claim 1, wherein the user interface is further configured to receive user input about at least one of patient positioning, user interface tooling or view layout selections or templates thereof, wherein user interface tooling and lay-out selections determine a lay-out of viewing settings on a viewing station.

12. The medical product as claimed in claim 5, wherein the data object further comprises instructions for the medical imaging system to reacquire one or more of the medical images based on a quality of the attenuation map generated by the attenuation map generation module.

13. A method for performing image based radiotherapy planning comprising:
receiving user input identifying a treatment target in a patient and a treatment technique for performing radiotherapy to treat the treatment target in the patient;
executing a data object comprising computer readable instructions based on at least one of the treatment target or the treatment technique, the instructions comprising image acquisition parameters, contour parameters, and treatment planning parameters;
receiving medical images of the patient according to the image acquisition parameters after the identifying of the treatment technique;
segmenting one or more contours based on one or more of the medical images according to the contour parameters, and
calculating a radiotherapy plan based on the one or more contours according to the treatment planning parameters.

14. The method of claim 13, wherein the radiotherapy plan is calculated based in response to receiving the user input without a need for further user interaction.

15. The method of claim 13, wherein receiving the medical images of the patient comprises acquiring magnetic resonance images, the method further comprising:
calculating an attenuation map based on one or more of the magnetic resonance images, wherein the radiotherapy plan is calculated further based on the attenuation map.

16. The method of claim 15, wherein receiving the magnetic resonance images comprises acquiring Dixon images and T2w images,
wherein segmenting the one or more contours is further based on an in-phase Dixon and a T2w image, and
wherein calculating the attenuation map is further based on the Dixon images.

17. The method of claim 16, further comprising:
reacquiring one or more of the medical images based on segmentation results provided by the contour module.

18. The method of claim 13, further comprising:
adapting the instructions based on at least one of the medical images, the one or more contours or the radiotherapy plan.

\* \* \* \* \*